United States Patent [19]
Jones

[11] Patent Number: 5,194,712
[45] Date of Patent: Mar. 16, 1993

[54] CUTTING TOOL USING A DIAMOND WINDOW

[76] Inventor: Barbara L. Jones, 80 Chisbury Close, Forest Park, Bracknell, RG12 3TX, England

[21] Appl. No.: 689,199

[22] Filed: Apr. 22, 1991

[30] Foreign Application Priority Data

Apr. 23, 1990 [GB] United Kingdom ............... 9009059

[51] Int. Cl.⁵ .................................. B23K 26/16
[52] U.S. Cl. ................... 219/121.67; 606/17
[58] Field of Search .............. 219/121.67, 121.72, 219/121.63, 121.64; 606/13–18

[56] References Cited

U.S. PATENT DOCUMENTS 4,383,728  5/1983  Litington ........................... 350/1.7
4,627,435 12/1986  Hoskin .......................... 219/233 X

OTHER PUBLICATIONS

Moravec, *The Journal of Vacuum Science Technology*, 20(3), Mar. 1982, pp. 338–340.

*Primary Examiner*—C. L. Albritton
*Attorney, Agent, or Firm*—Scully, Scott, Murphy & Presser

[57] ABSTRACT

A cutting tool such as a laser knife comprises a passage for a beam of light, a layer of single crystal diamond located in the passage to intercept the light passing down the passage, the diamond layer presenting a surface for the incoming light and a surface for the outgoing light, and an anti-reflective coating bonded to at least one of the surfaces. The anti-reflective coating is typically a silicon ceramic material for wavelengths not exceeding 2 μm and typically a polycrystalline diamond for wavelengths of at least 2 μm.

16 Claims, 2 Drawing Sheets

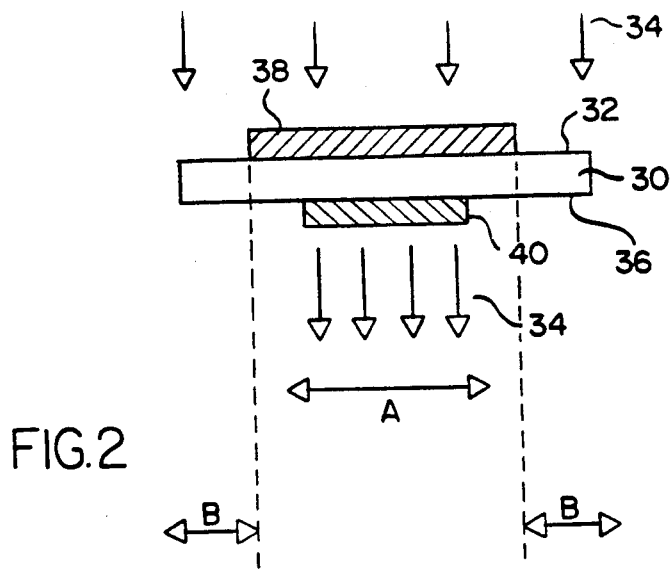
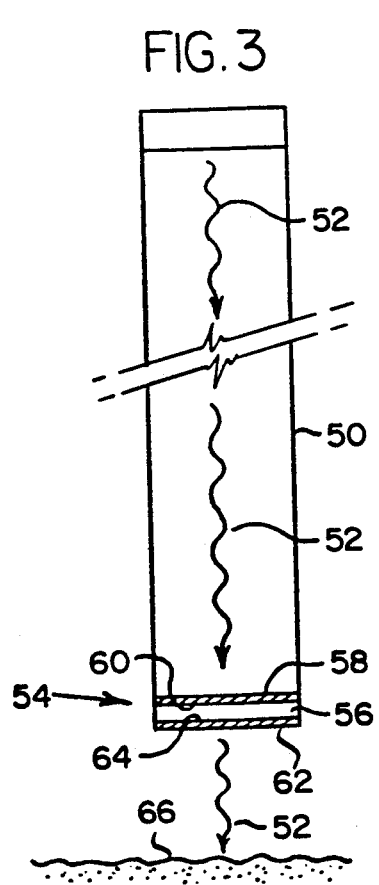
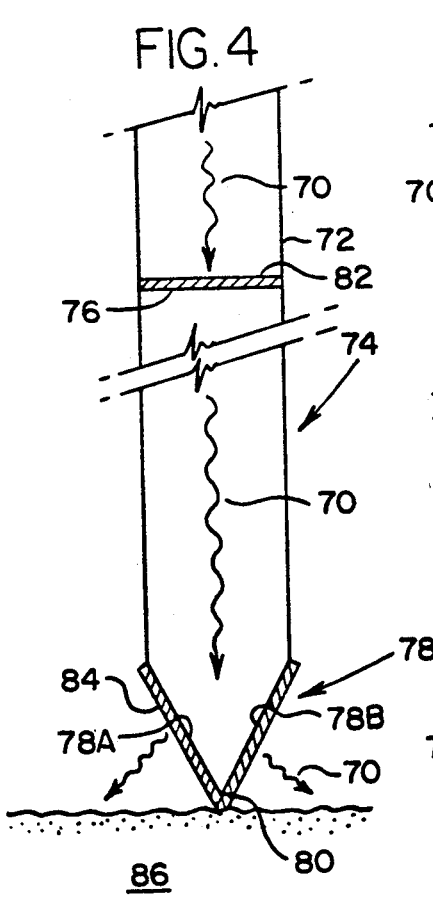
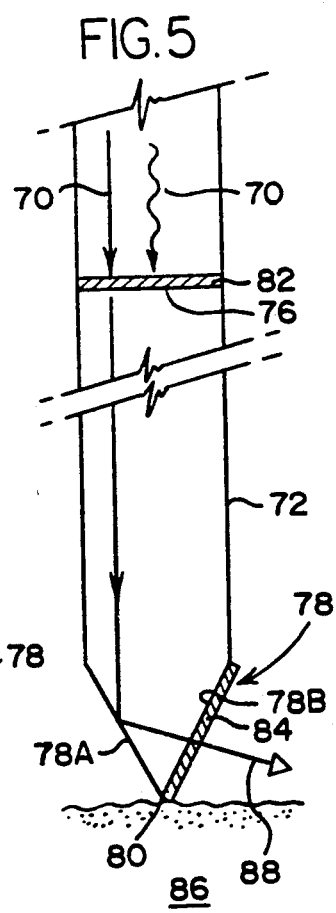

CUTTING TOOL USING A DIAMOND WINDOW

BACKGROUND OF THE INVENTION

This invention relates to a cutting tool using a diamond window.

Diamond is a material which is inert to a variety of hostile environments and also has excellent wear-resistant and abrasive properties, combined with high infrared transmission. Consequently, it is the ideal material to use in a variety of tools such as laser knives. Laser knives are used in delicate surgical operations and include a tube along which the laser beam is directed ending with a diamond window through which the laser beam passes.

The refractive indices of diamond and air are very different. Consequently, some of the laser beam does not pass through the diamond window and is reflected. The reflected laser beam can cause problems to the handler of the knife and the equipment itself, and diminishes the forward power available.

U.S. Pat. No. 4,383,728 describes a reflector of infrared radiation comprising a highly reflecting surface coated with a thin infrared transparent layer of glassy diamond-like carbon. The carbon layer may be formed directly on the surface or an initial thin bonding layer, e.g. of silicon or germanium, may be deposited on the reflecting surface followed by the carbon layer.

In an article entitled "The Development of Diamond-like (i-Carbon) Thin Films as Anti-reflecting Coatings for Silicon Solar Cells", 1982, American Vacuum Society, 338 to 340, T. J. Moravec and J. C. Lee describe the application of a diamond-like thin film to silicon as an anti-reflecting coating.

SUMMARY OF THE INVENTION

A cutting tool according to the invention comprises a passage for a beam of light, a layer of single crystal diamond located in the passage to intercept light passing down the passage, the diamond layer presenting a surface for the incoming light and a surface for the outgoing light, and an anti-reflective coating bonded to at least one of the surfaces.

BRIEF DESCRIPTION OF THE DRAWINGS

FIG. 2 is a sectional side view of another coated single crystal diamond layer useful in the invention, FIG. 3 is a schematic sectional side view of an embodiment of a cutting tool of the invention, FIG. 4 is a schematic sectional side view of a second embodiment of a cutting tool of the invention, and FIG. 5 is a schematic sectional side view of a third embodiment of a cutting tool of the invention.

DESCRIPTION OF EMBODIMENTS

Figure 1:
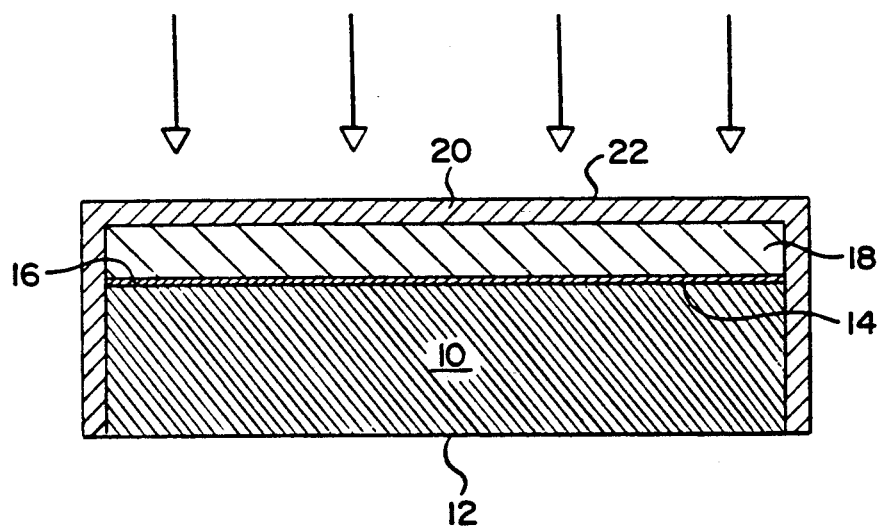
FIG. 1 is a sectional side view of a single crystal diamond, coated on one side only, useful in the invention.

An important feature of the invention is that at least a portion of either the light-incoming surface or light-outgoing surface or both of the single crystal diamond layer is provided with an anti-reflective coating. An anti-reflective coating is one which will reduce the reflection of the light beam as it passes through the single crystal diamond. In this way, more of the light beam passes through the single crystal diamond increasing the forward power or intensity of the beam. The invention has particular application to light beams which are laser beams.

An example of an anti-reflective coating for wavelengths not exceeding 2 μm is a silicon organic material such as silicon nitride, silicon oxynitride, silicon carbide, silicon oxide or the like. Such anti-reflective coatings do not adhere easily to diamond. Thus, it is preferred that the surface of the single crystal diamond layer to which the anti-reflective coating is bonded contains a minor amount, e.g. less than 100 parts of a million, of silicon. Such a surface may be achieved by growing a thin diamond layer epitaxially on the single crystal diamond surface using chemical vapour deposition, particularly the method described in European Patent Publication No. 0348026. The silicon-containing layer will typically have a thickness of less than 1000 angstroms and preferably about 500 angstroms.

The coating of a silicon inorganic material, may have a thin diamond layer applied to its outer surface to improve the wear-resistance thereof. Typically, this protective diamond layer will be very thin and will be applied by standard chemical vapour deposition methods.

The anti-reflective coating for wavelengths of at least 2 μm is a layer of polycrystalline diamond produced, for example, using chemical vapour deposition. The polycrystalline diamond layer will present a rough surface which can act as an anti-reflective coating depending on the wavelength of the light beam. The rough surface of the polycrystalline diamond layer will have a plurality of small projections which may be pointed or flat topped or both. Between the projections will be voids or spaces.

The optimum thickness of the anti-reflective layer may be determined by a known mathematical formula set out below:

$$N_f = \sqrt{N_{diamond} \times N_{air}}$$

$$N_f t = \lambda/4$$

wherein $N_f$ is the refractive index of the material
$N_{diamond}$ is the refractive index of diamond
$N_{air}$ is the refractive index of air
$\lambda$ is the wavelength of the incident light beam
$t$ is the layer thickness.

In one form of the invention, both the light-incoming and light-outgoing surface of the single crystal diamond are disposed essentially perpendicular to the direction of the light beam. Preferably, both the light-incoming and light-outgoing surfaces of the single crystal diamond will have an anti-reflective coating bonded to it. Alternatively, only a portion of at least one of the light-incoming and light-outgoing surfaces will have an anti-reflective coating applied to it. The effect of this arrangement is that the light beam of greater power or intensity will exit through the portion of the surface which has an anti-reflective coating applied to it. Hence a focussing arrangement can be achieved.

In another form of the invention, the light incoming surface of the single crystal diamond is disposed essentially perpendicular to the light beam and the light-outgoing surface is defined by two sloping surfaces meeting at a cutting edge which can function as a mechanical cutting edge. Thus, the use of such an arrangement, will result in cutting being achieved both mechanically through the cutting edge and optically by means of the laser beam. In this form of the invention, the entire light-outgoing surface may have an anti-reflective coating applied to it. Alternatively, if a region of high light intensity and a region of low light intensity is desired, then a portion only, e.g. one sloping surface only, may have an anti-reflective coating bonded to it.

Embodiments of the invention will now be described with reference to the accompanying drawings. Referring first to FIG. 1, there is shown a diamond window comprising a body 10 of single crystal diamond. The body 10 is of block shape having major flat surfaces 12, 14 on each of opposite sides thereof. A thin layer 16 of diamond is deposited on the surface 14 using the chemical vapour deposition method described in European Patent Publication No. 0 348 026. This method involves placing the substrate to be coated on a silicon nitride surface which covers completely a microwave energy sink. Using this method, silicon atoms are trapped in the diamond layer 16. The silicon atoms will be present in this layer in an amount of less than 100 parts per million. Thereafter, a layer 18 of silicon nitride is deposited on the diamond layer 16 using standard chemical vapour deposition techniques. This silicon nitride layer is firmly bonded to the single crystal diamond body 10 through the silicon-containing diamond layer 16. Good adhesion of the silicon nitride to the single crystal diamond is achieved.

An overlayer 20 of diamond may be provided. This overlayer is preferably deposited by chemical vapour deposition and is very thin, i.e. of the order of 110 angstroms in thickness. This overlayer provides a wear-resistant covering for the silicon nitride anti-reflective layer 18.

In use, a laser beam will be directed at the surface 22 in the direction of the arrows. The laser beam passes through the various layers and then out through the surface 12. On passage through the various layers, considerably less reflection takes place than would be the case without the anti-reflective silicon nitride layer 18.

FIG. 2 illustrates another embodiment of a diamond window useful in the invention. Referring to this figure, there is shown a layer 30 of single crystal diamond. The layer 30 presents one major surface 32 for the incoming laser beam 34 and another major surface 36 for the outgoing laser beam 34. An anti-reflective coating 38 is bonded to the surface 32 while an anti-reflective coating 40 is bonded to the surface 36. It is to be noted that neither coating 38 nor coating 40 covers the entire diamond surface to which it is bonded. This means that the laser beam passing through the diamond will have a region of maximum intensity indicated in the region A and regions of minimum intensity in the regions B.

An embodiment of a laser knife of the invention is illustrated by FIG. 3. Referring to this figure, a laser knife comprises a tube or passage 50 along which a laser beam 52 passes from a source (not shown) and a diamond window 54 located across the passage 50 to intercept the laser beam. The diamond window comprises a layer 56 of single crystal diamond having an anti-reflective coating 58 bonded to the major flat surface 60 thereof and an anti-reflective coating 62 bonded to the other major flat surface 64 thereof. The laser beam 52 exits through the surface 64 and the anti-reflective coating 62 and into a medium 66 to be cut by the laser beam. The cutting action is achieved solely by means of the laser beam.

In the embodiment illustrated by FIG. 3, both surfaces 60 and 64 have anti-reflective coatings bonded to them. It is possible to coat only one of these surfaces and still achieve an improvement over prior art laser knives.

FIG. 4 illustrates a second embodiment of a laser knife. Referring to this figure, a laser beam 70 passes down passage 72 where it is intercepted by a diamond knife 74. The diamond knife 74 is made of single crystal diamond and has a flat surface 76 perpendicular to the laser beam 70 and a surface 78 for the outgoing laser beam. The surface 78 has sloping portions or faces 78a and 78b which meet along cutting edge 80.

An anti-reflective coating 82 is applied to the surface 76 and an anti-reflective coating 84 is applied to the entire surface 78, i.e. both sloping faces.

The medium to be cut is indicated by the numeral 86. In cutting into the medium, cutting is achieved both by mechanical action of the edge 80 and by the laser beam 70. The high refractive index of diamond allows light to refract within the diamond between the surfaces 76 and 78. The anti-reflective coating applied to the surface 78 allows for maximum light power to emerge from the diamond.

The embodiment of FIG. 5 is similar to that of FIG. 4 and like parts carry like numerals. In this embodiment, the anti-reflective coating 84 is applied to one sloping face 78b only of the light-outgoing surface 78. Thus, in this embodiment, the laser beam will be reflected more from the uncoated surface than from the coated surface resulting in a concentration of the beam passing through the coated surface and in the direction of the arrow 88. A more intense cut can thus be achieved on one side of the knife relative to the other side.

In the laser knives described above, the nature of the anti-reflective coating will vary according to the wavelength of the laser beam. For example, if the wavelength of the laser beam is 1,06 μm then the preferred anti-reflective coating is a silicon inorganic material. If, on the other hand, the wavelength of the laser beam is 10,6 μm then the preferred anti-reflective coating is a polycrystalline diamond coating.

I claim:

1. A cutting tool comprising a passage for a beam of light, a layer of single crystal diamond located in the passage to intercept light passing down the passage, the diamond layer presenting a surface for the incoming light and a surface for the outgoing light, and an anti-reflective coating bonded to at least one of the surfaces.

2. A cutting tool according to claim 1 wherein the beam of light is a laser beam.

3. A cutting tool according to claim 1 wherein the anti-reflective coating is selected from silicon nitride, silicon oxynitride, silicon carbide and silicon oxide.

4. A cutting tool according to claim 3 wherein the anti-reflective coating is bonded to the single crystal diamond surface through a thin layer of diamond containing a minor amount of silicon.

5. A cutting tool according to claim 4 wherein the silicon is present in the diamond-bonding layer in an amount of less than 100 parts per million.

6. A cutting tool according to claim 4 wherein the bonding-diamond layer is applied to the diamond surface by chemical vapour deposition.

7. A cutting tool according to claim 3 wherein the bonding-diamond layer has a thickness of no more than 1000 angstroms.

8. A cutting tool according to claim 1 wherein the anti-reflective coating is a layer of polycrystalline diamond.

9. A cutting tool according to claim 8 wherein the polycrystalline diamond is produced by chemical vapour deposition.

10. A cutting tool according to claim 1 wherein both the light-incoming and light-outgoing surfaces are disposed essentially perpendicular to the direction of the light beam.

11. A cutting tool according to claim 10 wherein both the light-incoming and the light-outgoing surfaces of the single crystal diamond have anti-reflective coatings bonded to them.

12. A cutting tool according to claim 10 wherein only a portion of at least one of the light-incoming and the light-outgoing surfaces has an anti-reflective coating applied to it.

13. A cutting tool according to claim 1 wherein the light-incoming surface of the single crystal diamond is disposed essentially perpendicular to the light beam and the light-outgoing surface is defined by two sloping surfaces which meet at a cutting edge.

14. A cutting tool according to claim 13 wherein the entire light-outgoing surface has an anti-reflective coating applied to it.

15. A cutting tool according to claim 13 wherein one sloping surface only of the light-outgoing surface has an anti-reflective coating bonded to it.

16. A cutting tool according to claim 13 wherein the light-incoming surface has an anti-reflective coating applied to it.

* * * * *